United States Patent
Zhong et al.

(10) Patent No.: US 11,970,441 B2
(45) Date of Patent: Apr. 30, 2024

(54) METHOD FOR PREPARING THIONOCARBAMATE AND CO-PRODUCING 2-MERCAPTOETHANOL OR O-ALKYLTHIOETHYL XANTHATE

(71) Applicant: CENTRAL SOUTH UNIVERSITY, Changsha (CN)

(72) Inventors: Hong Zhong, Changsha (CN); Xiaoping Huang, Changsha (CN); Shuai Wang, Changsha (CN); Zhanfang Cao, Changsha (CN)

(73) Assignee: CENTRAL SOUTH UNIVERSITY, Changsha (CN)

( * ) Notice: Subject to any disclaimer, the term of this patent is extended or adjusted under 35 U.S.C. 154(b) by 826 days.

(21) Appl. No.: 16/977,107

(22) PCT Filed: Dec. 7, 2018

(86) PCT No.: PCT/CN2018/119879
§ 371 (c)(1),
(2) Date: Sep. 1, 2020

(87) PCT Pub. No.: WO2019/223290
PCT Pub. Date: Nov. 28, 2019

(65) Prior Publication Data
US 2021/0002218 A1    Jan. 7, 2021

(30) Foreign Application Priority Data
May 25, 2018   (CN) .......................... 201810519232.6

(51) Int. Cl.
C07C 333/04   (2006.01)
B03D 1/012    (2006.01)
C07C 329/14   (2006.01)

(52) U.S. Cl.
CPC ............ *C07C 333/04* (2013.01); *B03D 1/012* (2013.01); *C07C 329/14* (2013.01); *B03D 2201/02* (2013.01); *B03D 2203/02* (2013.01)

(58) Field of Classification Search
CPC ..... C07C 333/04; C07C 329/14; B03D 1/012; B03D 2201/02
See application file for complete search history.

(56) References Cited

U.S. PATENT DOCUMENTS 2,691,635 A * 10/1954 Harris .................. C07C 333/02
                                                      252/61
4,482,500 A    11/1984 Lewellyn
(Continued)

FOREIGN PATENT DOCUMENTS

CN    1169988 A     1/1998
CN    1548418 A    11/2004
(Continued)

OTHER PUBLICATIONS

"Machine Translation of CN106380434", Zhong et al., published Feb. 2017, 29 total pages. (Year: 2017).*
(Continued)

*Primary Examiner* — Jonathan M Peo
(74) *Attorney, Agent, or Firm* — Bayramoglu Law Offices LLC (57) ABSTRACT

The invention belongs to the field of mineral flotation collector materials, and particularly discloses a method for preparing thionocarbamate. In the preparation process, xanthate and 2-haloethanol are esterified to obtain O-alkyl-S-hydroxyethyl xanthate, and then O-alkyl-S-hydroxyethyl xanthate and fatty amine are reacted to obtain a mixture of thionocarbamate and 2-mercaptoethanol. The mixture of thionocarbamate and 2-mercaptoethanol is washed with alkali, and the oil phase and water phase are separated. The oil phase and water phase are thionocarbamate and 2-hy-
(Continued)

droxyethylthiolate, respectively, and 2-mercaptoethanol is obtained by washing with an acid. 2-alkylthioethanol is obtained by reacting 2-hydroxyethanethiolate with alkyl halide, and then with carbon disulfide and alkali to prepare O-alkylthioethyl xanthate. Thionocarbamate, 2-mercaptoethanol and O-alkylthioethyl xanthate prepared by this method possess high yield and high purity. The process is green and environmentally friendly, and is beneficial to the industrialization of co-production.

16 Claims, 8 Drawing Sheets

(56) References Cited

U.S. PATENT DOCUMENTS

| | | | |
|---|---|---|---|
| 4,659,853 A | | 4/1987 | Fu et al. |
| 5,041,599 A | | 8/1991 | Bishop et al. |
| 5,094,746 A | * | 3/1992 | Bush ................ B03D 1/012 252/61 |
| 5,759,760 A | | 6/1998 | Lushington et al. |
| 6,184,412 B1 | | 2/2001 | Kulkarni et al. |

FOREIGN PATENT DOCUMENTS

| | | |
|---|---|---|
| CN | 102690218 A | 9/2012 |
| CN | 104761579 A | 7/2015 |
| CN | 104817480 A | 8/2015 |
| CN | 106380434 A | 2/2017 |
| CN | 106380435 A | 2/2017 |
| CN | 108569989 A | 9/2018 |
| DE | 2408550 A1 | 2/1975 |
| EP | 0131374 A1 | 1/1985 |
| RU | 2661634 C1 | 7/2018 |

OTHER PUBLICATIONS 159350-07-09, Registry, STN on the web, Dec. 6, 1994. / 860178-53-6, Registry, STN on the web, Aug. 15, 2005.
96942-14-2, Registry, STN on the web, Jul. 1, 1985.
Takashi Ogata et al., Neutral 1,4-Bis(3-thiapentylxanthato)butane as Sensing Material for Samarium(III) Ion, Chemistry Letters, 1995, pp. 1041-1042.
Renaud Nicolay, Synthesis of Well-Defined Polythiol Copolymers by RAFT Polymerization, Macromolecules, 2012, pp. 821-827, vol. 45.
Preeti L. Pant et al., Deep Eutectic Solvent: An Efficient and Recyclable Catalyst for Synthesis of Thioethers, Chemistry Select, 2017, pp. 7645-7650, vol. 2, Issue 25.
A. K. Livshits et al., Effect of solid phase on foam stability, Tsvetnye Metally (Moscow, Russian Federation), 1960, pp. 23-26, vol. 33, No. 11.
Y. J. Shi et al., Analysis of Xanthate Derivatives by Vacuum Ultraviolet Laser-Time-of-Flight Mass Spectrometry, Analytical Chemistry, 1998, pp. 4534-4539, vol. 70, No. 21.
Xianghui Zeng, Development on Processesfor Synthesis of Thionocarbamate and its Byproducts, 2003, pp. 1-63.
Dai Hongyi et al., Preparation of isopropyl ethylthionocarbamate, Modern Chemical Industry, 1999, pp. 27-29, 19(1).
Johanna A.W. Verhagen et al., New nickel complexes with an S4 coordination sphere; synthesis, characterization and reactivity towards nickel and iron compounds, Inorganica Chimica Acta, 2004, pp. 2687-2693, 357.

* cited by examiner

METHOD FOR PREPARING THIONOCARBAMATE AND CO-PRODUCING 2-MERCAPTOETHANOL OR O-ALKYLTHIOETHYL XANTHATE

CROSS REFERENCE TO THE RELATED APPLICATIONS

This application is the national phase entry of International Application No. PCT/CN2018/119879, filed on Dec. 7, 2018 (WIPO Publication No. WO 2019/223290, publication date Nov. 28, 2019), which is based upon and claims priority to Chinese Patent Application No. 201810519232.6, filed on May 25, 2018, the entire contents of which are incorporated herein by reference.

TECHNICAL FIELD

The invention belongs to the technical field of mineral floatation, and particularly relates to a method for preparing a thionocarbamate and co-producing 2-mercaptoethanol and a novel O-alkylthioethyl xanthate collector.

BACKGROUND

With the increasing exploitation of mineral resources, the ore is becoming increasingly poor, fine and various, making the recovering of the useful minerals difficult. As an important technology of mineral recovery, froth flotation changes the physical and chemical properties of mineral surface by adding flotation reagents, which results in that the mineral particles with hydrophobicity are enriched in a foam layer, and the mineral particles with hydrophilicity are deposited at the bottom of a flotation separator, thereby realizing the separation of the minerals. Flotation collector is the key technology for efficient development and utilization of minerals. Since Keller used xanthate as a flotation collector for sulfide ore for the first time in 1925, xanthate has become the most important flotation collector for sulfide ore, and it is still the most widely used flotation collector for sulfide ore. Thionocarbamate (thiocarbamate) is a sulfide ore flotation collector with better selectivity than xanthate and aerofloat, which can realize mineral flotation separation in the lower pH medium, and it has been widely used in sulfide ore flotation with great potential applications.

There are many synthesis methods for thionocarbamate, including a one-step catalytic synthesis process, an isothiocyanate process, a dimethyl sulfate process and the process of esterification and ammonolysis of xanthate (Development on Processes for Synthesis of Thionocarbamate and its Byproducts [D]. Central South University 2003). Although the one-step catalytic synthesis process has the advantages of simple operation and fewer reaction steps, the yield of the product is not high, the economic value of the by-products is low, and catalysts such as nickel sulfate and palladium chloride have high solubility, which completely enter the water phase during the reaction, and are difficult to recover. Moreover, a large amount of industrial wastewater is produced, which pollutes the environment. Therefore, this process is rarely used to prepare thionocarbamate products in industry (the U.S. Pat. No. 5,041,599, German patent DE2408550). The isothiocyanate process (the U.S. Pat. Nos. 4,482,500, 4,659,853 and 6,184,412; the China patent CN1548418A) has not been widely used, in which thiocyanate used as a raw material was reacted with an organic halide to obtain an intermediate isothiocyanate prior to alcoholysis to give the thionocarbamate product. The process is complex, with many reaction steps and low product yield. Moreover, a small amount of organic intermediates and phase transfer catalyst are dissolved in the water phase, which causes certain pollution to the environment. The dimethyl sulfate process (the China patent CN1169988A) has the advantages of simple operation and high reaction efficiency. However, due to the instability of dimethyl sulfate, it will be rapidly hydrolyzed into sulfuric acid and methanol in water, which makes it difficult to popularize in practical production. Moreover, the absorption and reuse of methyl mercaptan are also difficult. For the process of esterification and ammonolysis of xanthate (the U.S. Pat. No. 2,691,635, Dai Hongyi, Wang Meijun, Preparation of Ethionine Ester [J]. Modern Chemical Industry, 1999, 19(1): 27-29) uses xanthate and sodium chloroacetate as raw materials for the esterification reaction, and then the obtained intermediate product reacts with primary amine for the ammonolysis reaction. The process has enough raw materials, simple process and easy mastering of production technology. However, in the practical production, the by-product of sodium thioglycolate dissolves in the water phase, which is difficult to recycle and causes a series of environmental problems.

The 2-mercaptoethanol was widely used in fine chemical, due to the molecular structure containing both mercapto and hydroxyl groups. The 2-mercaptoethanol was not only an important intermediate for pesticide, but also a stable component in a metal corrosion inhibitor, as well as a metal deactivator in a catalyst for catalytic cracking of heavy oil. Meanwhile, the 2-mercaptoethanol with high purity can be used as the raw material in the pharmaceutical and the photochemical industry, and was also widely applied as auxiliaries in industries such as rubber, textile and paint. The synthetic routes of 2-mercaptoethanol include a chloroethanol route, an ethylene oxide route and a hydrogen sulfide route. However, the method of preparing thionocarbamate with alkyl xanthate, haloethanol and fatty amine as raw materials and co-producing 2-mercaptoethanol has not been reported.

O-alkylthioethanol was an important pharmaceutical intermediate, and there are few reports on its preparation methods. Johanna used benzyl mercaptan and chloroethanol as raw materials in the presence of sodium hydroxide to prepare 2-hydroxyethyl (Johanna A, Michela B, Anthony L, et al, Inorg. Chim. Acta. 2004, 357:2687-2693), but it was obviously disadvantageous for the method that the benzyl mercaptan had an unpleasant odor.

SUMMARY

In order to solve the problems in the prior art, a first objective of the present invention is to provide a method for preparing a thionocarbamate, which aims to efficiently prepare a thionocarbamate and co produce 2-mercaptoethanol with high economic added value.

A second objective of the present invention is to co-produce an O-alkylthioethyl xanthate collector with a novel structure by further utilizing 2-mercaptoethanol prepared by the preparation method of the thionocarbamate.

A third objective of the present invention is to provide an O-alkylthioethylxanthate collector with a novel structure.

In order to achieve the above technical objectives, the present invention provides a method for preparing a thionocarbamate, and the method includes the following specific steps:

step 1): esterification reaction of a xanthate having a structure shown in formula I with 2-haloethanol to obtain an O-alkyl/alkylthioethyl-S-hydroxyethyl xanthate (also called an esterification product in the present invention) having a structure shown in formula II;

step 2): aminolysis reaction of the O-alkyl/alkylthioethyl-S-hydroxyethyl xanthate with a fatty amine shown in formula III to obtain a mixture of a thionocarbamate shown in formula IV and 2-mercaptoethanol;

step 3): washing the mixture of the thionocarbamate and the 2-mercaptoethanol with an alkali for separation of the thionocarbamate product as the oil phase from 2-hydroxyethyl thiolate as the aqueous phase;

Formula I

Formula II

Formula III

Formula IV in formula I to formula IV, $R^1$ is $C_1$ to $C_{16}$ alkyl, $C_1$ to $C_{16}$ aryl, or alkylthioethyl shown in formula V;

Formula V in formula V, $R^3$ is $C_1$ to $C_{16}$ alkyl or $C_6$ to $C_{16}$ aryl; and $R^2$ is $C_1$ to $C_8$ alkyl; and M is $Na^+$, $K^+$ or $NH_4^+$.

Preferably, $R^1$ is ethyl, propyl, isopropyl, butyl, isobutyl, sec-butyl, tert-butyl, pentyl, isopentyl, sec-pentyl, neopentyl, n-hexyl, isohexyl, sec-hexyl, n-octyl, isooctyl, phenyl, benzyl, phenethyl or dodecyl; and $R^2$ is methyl, ethyl, n-propyl, isopropyl, butyl, isobutyl, tert-butyl, pentyl, hexyl, phenyl or benzyl.

Halogenated elements of 2-haloethanol, for example, are Cl, Br and the like; and the halogenated elements of 2-haloethanol are preferably 2-chloroethanol or 2-bromoethanol.

In a preferable scheme, in step 1), after the esterification reaction of xanthate and the 2-haloethanol is completed, oil and water are separated. The oil phase is O-alkyl/alkylthioethyl-S-hydroxyethyl xanthate having a structure shown in formula II, and the synthetic route is shown in equation (1):

(1)

in equation (1), X is Cl or Br.

In a more preferable scheme, the molar ratio of the xanthate to the 2-haloethanol is 1.0:(0.9-1.2).

In a more preferable scheme, water is used as a solvent in the esterification reaction. On one hand, water is widely available and cheap; and on the other hand, xanthate and 2-haloethanol which are used as raw materials can be dissolved in water, so that the reaction is homogeneous. Moreover, O-alkyl/alkylthioethyl-S-hydroxyethyl xanthate generated by the reaction is insoluble in water, so that the high-quality O-alkyl/alkylthioethyl-S-hydroxyethyl xanthate can be obtained through simple oil-water separation.

In a further preferable scheme, the amount of the solvent water is 0 to 50 ml of water/1 mol (preferably 1 to 50 ml of water/1 mol) of xanthate.

In a more preferable scheme, the conditions of the esterification reaction are as follows: the reaction temperature is 20-100° C., and the reaction time is 1-8 h.

In the present invention, 2-haloethanol is used for replacing raw materials such as halogenated acetic acid in the prior art, and the raw materials are easy to hydrolyze under an alkaline condition and have slightly weaker activity than chloroacetic acid. The 2-haloethanol is firstly added into the reaction flask at room temperature, then xanthate is added in batches, after a period of reaction, solvent water is added, and then the mixture is heated to a set temperature for reaction. This operation sequence is helpful to ensure the efficiency of the reaction.

Further preferably, the 2-haloethanol and the xanthate are reacted in advance at 20-30° C. for 1-2 h, then water is added, and reaction is carried out at 20-100° C. Under the preferable conditions, defects of easiness in hydrolysis and low activity in the preparation process of the 2-haloethanol are further overcome, the preparation effect can be further improved, and the yield of the product is increased.

Preferably, in step (2), O-alkyl/alkylthioethyl-S-hydroxyethyl xanthate, shown in formula II, reacts with the fatty amine to obtain a mixture of a thionocarbamate and 2-hydroxyethyl thiolate having a structure shown in formula IV, and the synthetic route is shown in equation (2);

(2)

the fatty amine is primary fatty amine; preferably, in formula III, $R^2$ is $C_1$ to $C_8$ alkyl; and further preferably, $R^2$ is methyl, ethyl, n-propyl, isopropyl, butyl, isobutyl, tert-butyl, pentyl, hexyl, phenyl or benzyl.

In a more preferably scheme, the addition amount of the fatty amine is 0.9 to 1.2 times the molar weight of the O-alkyl/alkylthioethyl-S-hydroxyethyl xanthate.

Preferably, the conditions of ammonolysis reaction in step 2) are as follows: the reaction temperature is 30-100° C., and the reaction time is 1-6 h.

The mixture which is obtained in step 2) is washed with alkali liquor, and 2-mercaptoethanol can react with alkali to produce 2-hydroxyethyl thiolate ($HO-CH_2-CH_2-SM$); and M is a cation of the adopted alkali, preferably $Na^+$ or $K^+$; or $NH_4^+$.

In a preferable scheme, in step 3), the conditions of alkali washing are as follows: the concentration of alkali is 0.1-5 mol/L, and alkali washing times are 1-5 times.

In order to realize the utilization of the byproduct of 2-hydroxyethyl thiolate, the present invention also provides a method for preparing 2-mercaptoethanol, that is, 2-hydroxyethyl thiolate is subjected to acid washing to obtain the 2-mercaptoethanol product, and the specific route is shown in equation (3).

(3)

Preferably, the acid is hydrochloric acid or sulfuric acid; and the acid is preferably hydrochloric acid.

In a preferable scheme, the conditions of acid washing are as follows: the concentration of the acid is 0.01-5 mol/L.

The process has good economy, and the obtained by-product 2-mercaptoethanol can be directly separated and sold, and a novel xanthate can be further synthesized for recycling.

According to the technical scheme, the present invention also provides a method for preparing a thionocarbamate and co-producing O-alkylthioethyl xanthate. The method includes: the 2-hydroxyethanethiolate obtained in step 3) of the method for preparing thiocarbamate is subjected to thioalkylation reaction with alkyl halide with the structure of formula VI to obtain 2-alkylthioethanol with the structure of formula VII; reacting the 2-alkylthioethanol with carbon disulfide and alkali to obtain the O-alkylthioethyl xanthate shown in formula VIII.

(4)

(5)

where $R^1$ is $C_1$ to $C_8$ alkyl and aryl or alkylthioethyl shown in formula V; X is Cl, Br or I; and M is a cation of alkali, preferably $Na^+$ or $K^+$; or $NH_4^+$.

In the present invention, an aqueous solution of the 2-hydroxyethyl thiolate obtained in step 3) is fully utilized to directly react with the alkyl halide, the 2-alkylthioethanol is obtained through liquid separation, and the synthetic route is shown in equation (4). The O-alkylthioethyl xanthate with a novel structure and application as well as a structure shown in formula VIII is obtained through the reaction of the 2-alkylthioethanol, the carbon disulfide and the alkali, and the synthetic route is shown in equation (5).

Formula VI

Formula VII

Formula VIII

Preferably, the 2-hydroxyethyl thiolate is sodium 2-hydroxyethyl thiolate or potassium 2-hydroxyethyl thiolate.

Preferably, in formula VI, IV is preferably $C_1$ to $C_8$ alkyl or aryl; and further preferably, $R^1$ is ethyl, propyl, isopropyl, butyl, isobutyl, tert-butyl, n-pentyl, isopentyl, n-octyl, isooctyl, phenyl, benzyl or phenethyl.

In formula VI, X is preferably Cl or Br.

In a preferable scheme, the conditions of thioalkylation reaction are as follows: the reaction temperature is 5-50° C., and the reaction time is 0.5-3 h.

In a preferable scheme, the addition amount of the alkyl halide is 0.8 to 1.3 times the molar weight of the 2-hydroxyethyl thiolate.

In a preferable scheme, the reaction conditions of the 2-alkylthioethanol, the carbon disulfide and the alkali are as follows: the reaction temperature is 10-40° C., and the reaction time is 1-6 h.

In a preferable scheme, the molar ratio of raw materials is as follows: 2-alkylthioethanol:$CS_2$:alkali metal hydroxide=1.0:(1.0-5.0):(0.9-1.2).

Preferably, the alkali is NaOH, KOH or $NH_3 \cdot H_2O$.

In formula VIII, the type of the obtained O-alkylthioethyl xanthate can by determined and selected through the type of the added alkali. For example, when the adopted alkali is sodium hydroxide, sodium O-alkylthioethyl xanthate is obtained. In a similar way, required potassium salt or ammonium salt can be obtained.

The reaction route of the method for preparing the thionocarbamate and co-producing the 2-mercaptoethanol or the O-alkylthioethyl xanthate in the present invention is shown in equation (6), and the method includes the following specific steps:

(6) reacting xanthate and 2-haloethanol to prepare O-alkyl/alkylthioethyl-S-hydroxyethyl xanthate (an esterification product);

(7) reacting the O-alkyl/alkylthioethyl-S-hydroxyethyl xanthate with a fatty amine to obtain a mixture of a thionocarbamate and 2-mercaptoethanol;

(8) after alkali washing of the mixture of the thionocarbamate and the 2-mercaptoethanol, standing, separating the oil phase from the aqueous phase, in which the oil phase and the aqueous phase are respectively a high-purity thionocarbamate product and 2-hydroxyethyl thiolate, and carrying out acid washing to obtain a 2-mercaptoethanol product;

(9) reacting the 2-hydroxyethyl thiolate with alkyl halide to obtain a 2-alkylthioethanol product.

(10) reacting the 2-alkylthioethanol with carbon disulfide and alkali to obtain an O-alkylthioethyl xanthate product.

(6)

It is found that the O-alkyl/alkylthioethyl-S-hydroxyethyl xanthate with the structure shown in formula II is used as a flotation collector for flotation of nonferrous metal sulfide ores in nonferrous metal ores.

The novel application of the compound with the structural formula shown in formula II in the field of mineral flotation is developed in the present invention, and it is found that the compound shows excellent flotation performance in the field of mineral flotation. O-alkyl/alkylthioethyl-S-hydroxyalkyl xanthate compound, having the groups of xanthic acid and hydroxyl, used as a flotation collector not only showed good collecting selectivity, but also had good foaming performance.

The present invention further provides a novel O-alkyl-thioethyl xanthate collector in which $R^1$ is alkylthioethyl structure as shown in formula VIII.

The present invention provides the application of a novel compound having a structure as shown in formula VIII, and the compound is used as a flotation collector to be applied to flotation of metallic minerals.

The key of the technical scheme of the present invention is that 2-hologenated ethanol (also known as 2-haloethanol) is adopted to replace conventional chloroalkane or chloroacetic acid to be subjected to esterification reaction with xanthate to be converted into an O-alkyl/alkylthioethyl-S-hydroxyethyl xanthate intermediate product, the O-alkyl/alkylthioethyl-S-hydroxyethyl xanthate is converted into a thionocarbamate and 2-mercaptoethanolate through the ammonolysis reaction, and alkali washing is carried out to obtain the high-purity thionocarbamate and 2-hydroxyethyl thiolate. Acid washing is carried out on the aqueous solution of 2-hydroxyethyl thiolate to obtain the 2-mercaptoethanol. Compared with the existing thionocarbamate synthesis method, this method has the obvious advantages that 1) thionocarbamate and the 2-mercaptoethanol can be well separated by alkali washing, which avoids repeated acid washing and alkali washing, distillation or extraction separation in traditional process, the process is simple to operate, and the obtained 2-mercaptoethanol is a product with great application prospect; and 2) the whole process can obtain high-purity thionocarbamate products, and O-alkyl/alkylthioethyl-S-hydroxyethyl xanthate with high-efficiency collecting ability toward sulfide ore, and the waste water only contains sodium chloride, which is green and environmentally friendly. According to the technical scheme of the present invention, 2-mercaptoethylthiolate, which is obtained as a byproduct of a thionocarbamate process, firstly reacts with the alkyl halide to prepare 2-alkylthioethanol, and then, 2-alkylthioethanol reacts with the carbon disulfide and the alkali to synthesize O-alkylthioethyl xanthate collector with a brand-new structure, and the byproduct O-alkylthioethyl xanthate can be recycled as a raw material.

Beneficial Effect

According to the technical scheme of the present invention, wastewater containing a small amount of xanthate and sodium chloride generated by the esterification reaction of the xanthate and 2-haloethanol is directly used for flotation operation, so that the wastewater is fully utilized, and the wastewater is reduced.

According to the technical scheme of the present invention, the xanthate and the 2-haloethanol are used as initial raw material, a high-purity thionocarbamate product, 2-mercaptoethanol and flotation collectors O-alkyl/alkylthioethyl-S-hydroxyethyl xanthate and O-alkylthioethyl xanthate are obtained simultaneously, and the purpose of obtaining multiple high-added-value products through one process is achieved.

According to the technical scheme of the present invention, the method is simple to operate, product separation can be achieved only through simple oil-water separation, and the production cost is greatly reduced. The method has the characteristics of simplicity in operation, high raw material utilization rate, environmental friendliness and the like, and the O-alkylthioethyl xanthate generated in the synthesis process can be recycled, so that industrial application is expected to be realized.

DETAILED DESCRIPTION OF THE EMBODIMENTS

The present invention is further illustrated by, but not limited to, the following examples. All parts and percentages in the examples refer to mass, unless otherwise specified.

Figure 1:
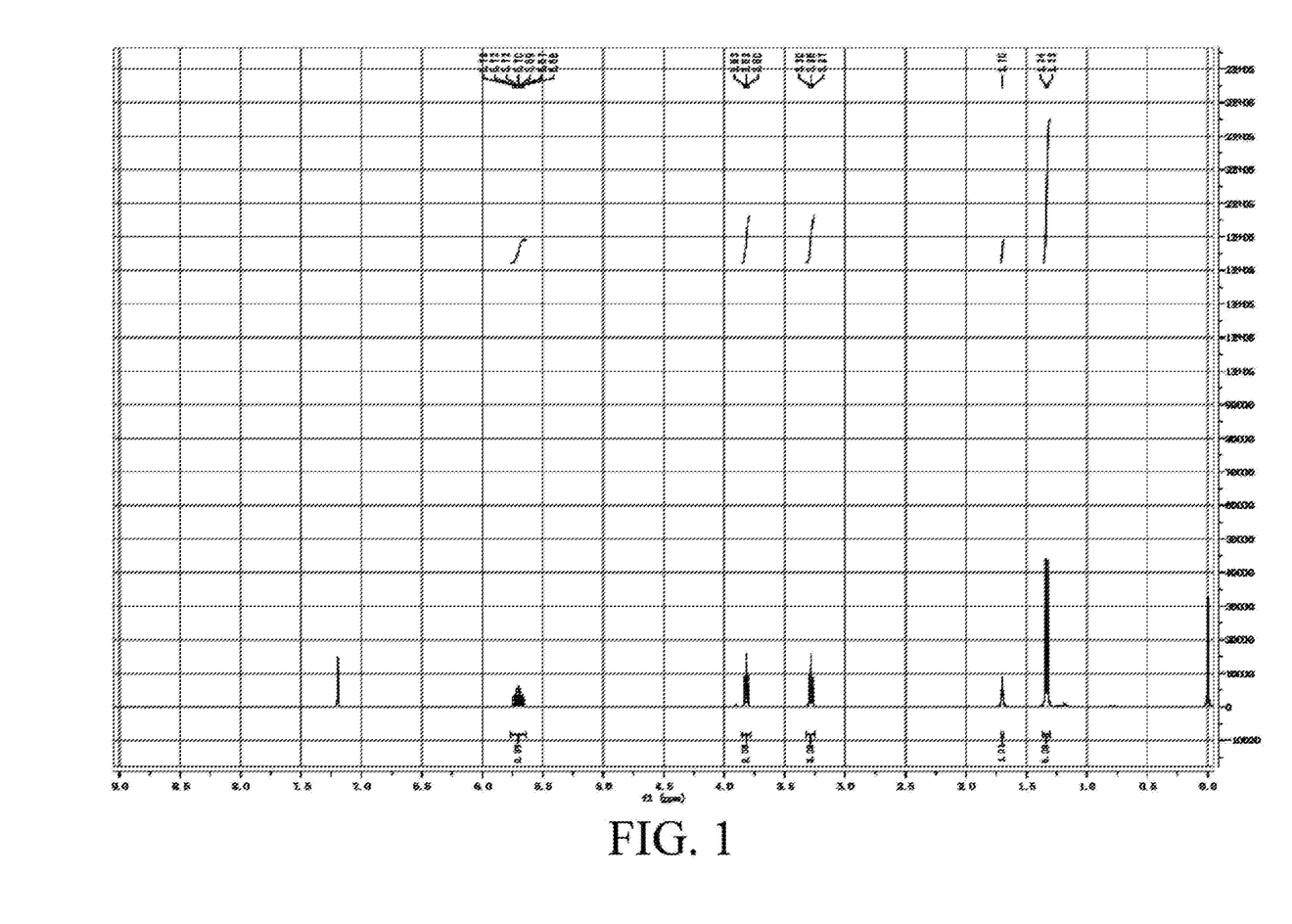
FIG. 1 is a $^1$H NMR of O-isopropyl-S-hydroxyethyl xanthate.
Figure 6:
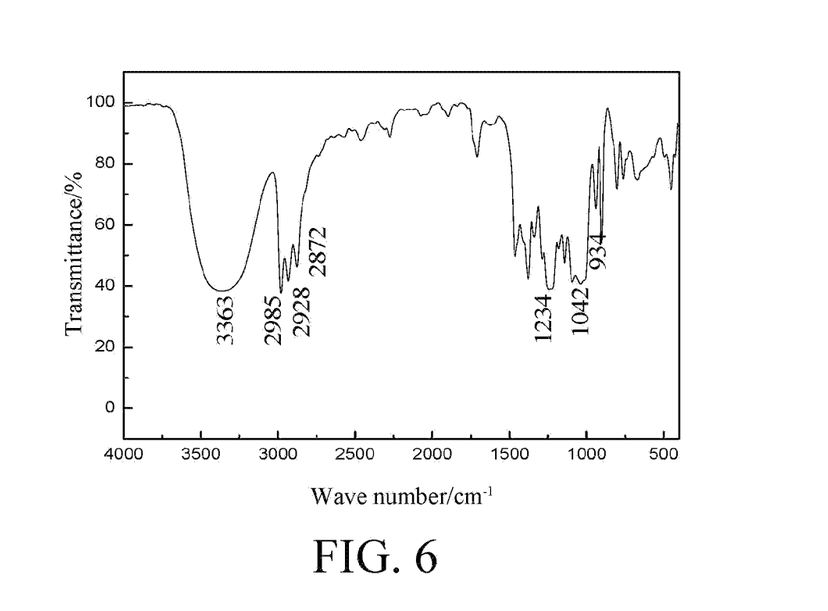
FIG. 6 is an infrared spectrogram of O-isopropyl-S-hydroxyethyl xanthate.

Example 1: Preparation of O-isopropyl-S-hydroxyethyl xanthate 8.13 parts of 2-chloroethanol with the purity of 99% are added into a reactor, 18.9 parts of sodium isopropyl xanthate with the purity of 83.54% are added in batches while stirring is conducted, then 15 parts of distilled water are added, the temperature is increased until the temperature in the reactor reaches 60° C., the mixture is cooled to the room temperature after a constant-temperature reaction is conducted for 5 h, liquid separation is conducted to obtain an oil phase O-isopropyl-S-hydroxyethyl xanthate, and analysis shows that the yield of the O-isopropyl-S-hydroxyethyl xanthate is 88.3%. The product is characterized after being purified by column chromatography, $^1$H NMR of the O-isopropyl-S-hydroxyethyl xanthate is shown in FIG. 1, and an infrared spectrogram is shown in FIG. 6.

Figure 2:
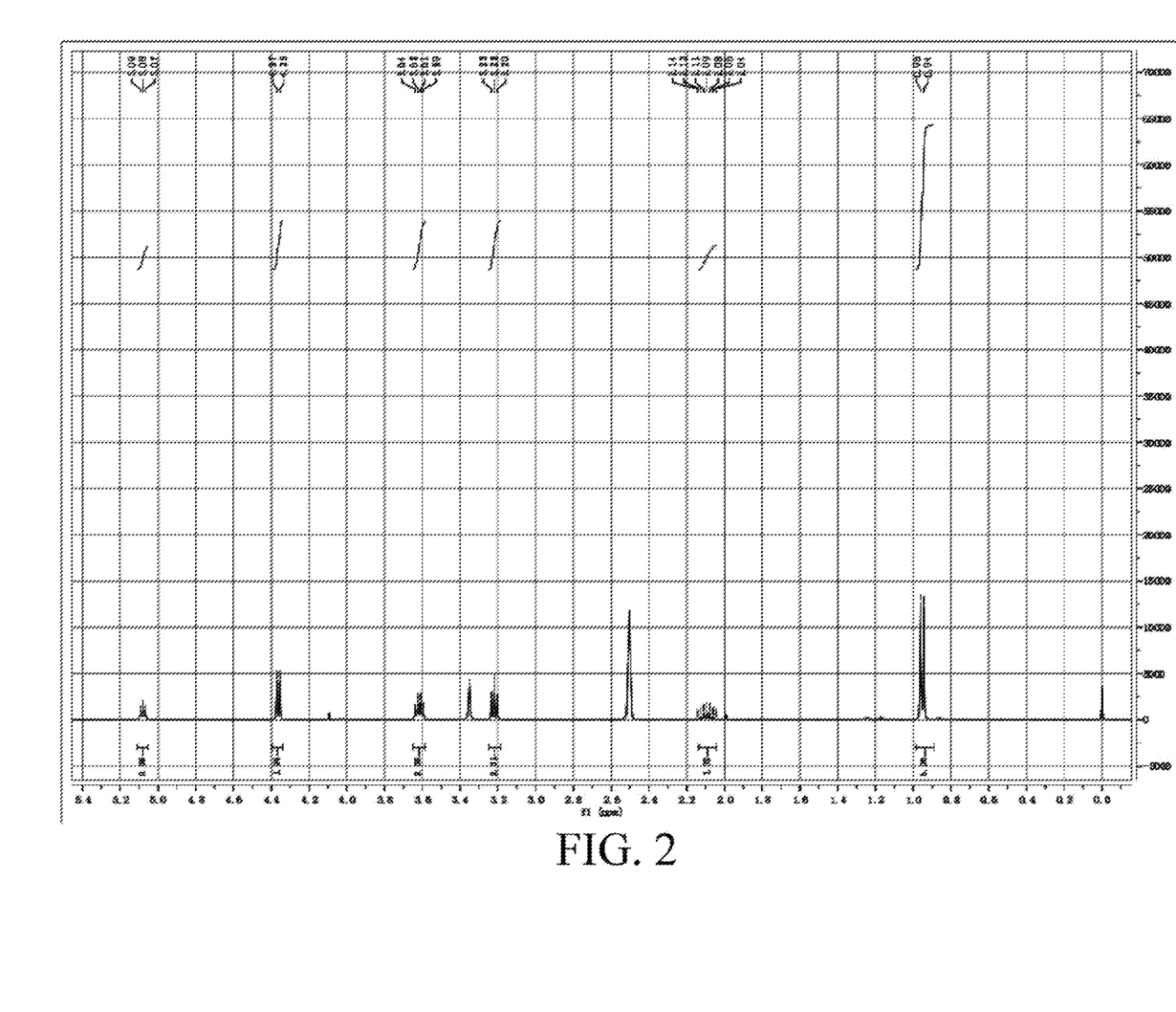
FIG. 2 is a $^1$H NMR of O-isobutyl-S-hydroxyethyl xanthate.
Figure 7:
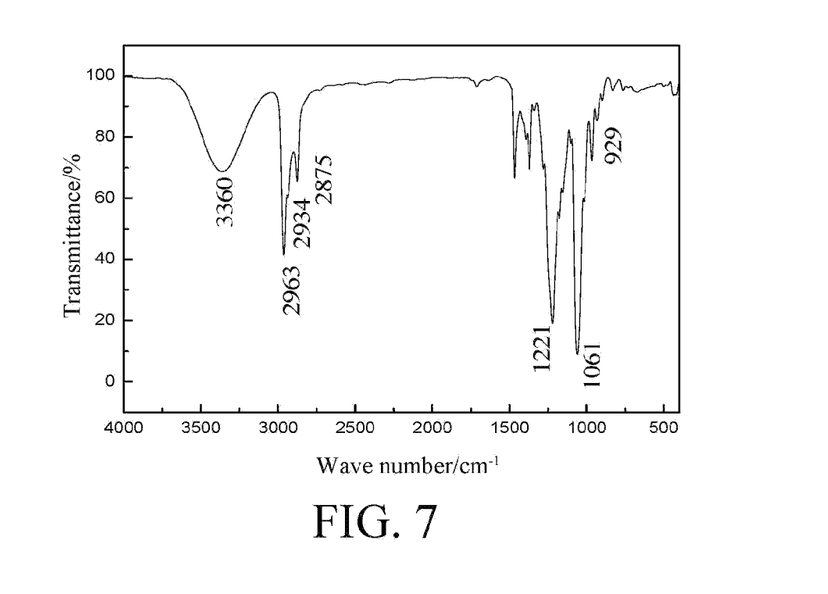
FIG. 7 is an infrared spectrogram of O-isobutyl-S-hydroxyethyl xanthate.

Example 2: Preparation of O-isobutyl-S-hydroxyethyl xanthate 8.13 parts of 2-chloroethanol with the purity of 99% are added into a reactor, 19.32 parts of sodium isobutyl xanthate with the purity of 89.0% are added in batches while stirring is conducted, then 15 parts of distilled water are added, the temperature is increased until the temperature in the reactor reaches 50° C., the mixture is cooled to the room temperature after a constant-temperature reaction is conducted for 7 h, liquid separation is conducted to obtain an oil phase O-isobutyl-S-hydroxyethyl xanthate, and analysis shows that the yield of the O-isobutyl-S-hydroxyethyl xanthate is 78.2%. The product is characterized after being purified by column chromatography, $^1$H NMR of the O-isobutyl-S-hydroxyethyl xanthate is shown in FIG. 2, and an infrared spectrogram is shown in FIG. 7.

Figure 5:
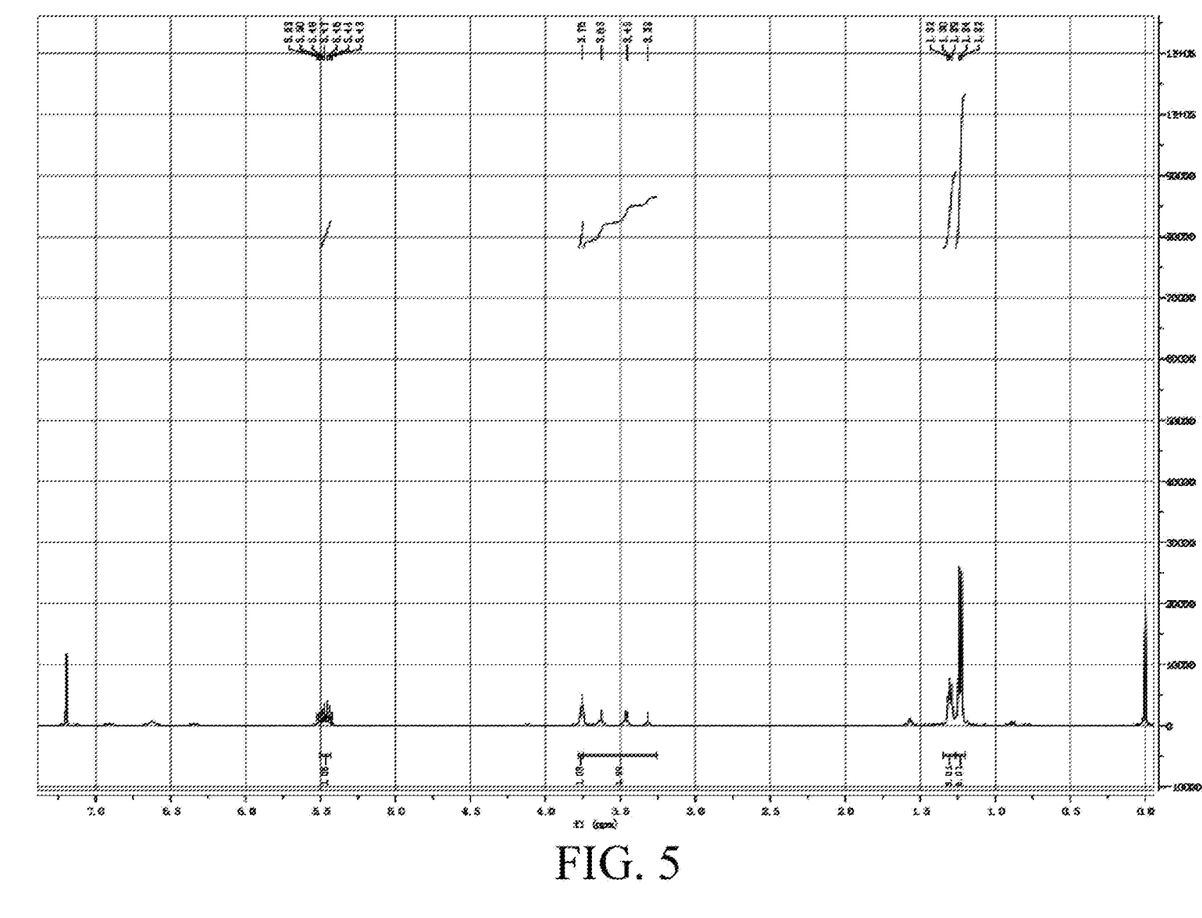
FIG. 5 is a NMR of O-isopropyl-N-ethylthiocarbamate.
Figure 9:
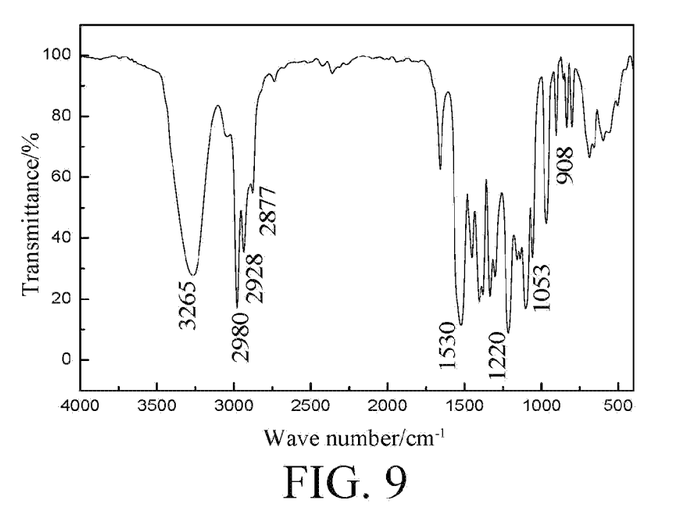
FIG. 9 is an infrared spectrogram of O-isopropyl-N-ethylthiocarbamate.

Example 3: Preparation of O-isopropyl-N-ethylthiocarbamate and 2-mercaptoethanol The oil phase obtained in example 1 is transferred into a reactor, 7 parts of ethylamine aqueous solution (the content is 65-70%) are added into a constant-pressure dropping funnel at the temperature of 20° C. or below, the temperature is raised to be 70° C., reaction lasts for 1 hour, the product is cooled to room temperature, reaction liquid is washed with 50 parts of a sodium hydroxide solution with the concentration of 8.3%, and liquid separation is carried out to obtain an oil phase which is O-isopropyl-N-ethylthiocarbamate with the purity of 96.7%, the yield based on the O-isopropyl-S-hydroxyethyl xanthate is 85.7%, the aqueous phase is sodium 2-hydroxyethyl thiolate, the purity is 28.097%, the yield based on the O-isopropyl-S-hydroxyethyl xanthate is 98.1%, 50 parts of a hydrochloric acid solution with the concentration of 10.95% are added into the aqueous phase, and acidifying is carried out at normal temperature for 2 h to obtain a 2-mercaptoethanol product with the yield of 92.34%. The product is characterized after being purified by column chromatography, $^1$H NMR of the O-isopropyl-N-ethylthiocarbamate is shown in FIG. 5, and an infrared spectrogram is shown in FIG. 9.

Example 4: Preparation of O-isobutyl-N-ethylthiocarbamate and 2-mercaptoethanol The oil phase obtained in example 2 is transferred into a reactor, 7 parts of ethylamine aqueous solution (the content is 65%-70%) are added into a constant-pressure dropping funnel at the temperature of 20° C. or below, the temperature is raised to 70° C., the reaction lasts for 1 hour, the reaction product is cooled to room temperature, reaction liquid is washed with 50 parts of sodium hydroxide solution with the concentration of 8.3%, liquid separation is carried out to obtain an oil phase which is O-isobutyl-N-ethylthiocarbamate with the purity of 95.3%, the yield based on O-isobutyl-S-hydroxyethyl xanthate is 82.7%, the aqueous phase is sodium hydroxyethyl thiolate with the purity of 27.97%, and the yield based on O-isopropyl-S-hydroxyethyl xanthate is 97.9%. 50 parts of hydrochloric acid solution with the concentration of 10.95% are added into the aqueous phase, and acidifying is carried out at normal temperature for 2 h to obtain the 2-mercaptoethanol product with the yield of 90.34%.

Figure 3:
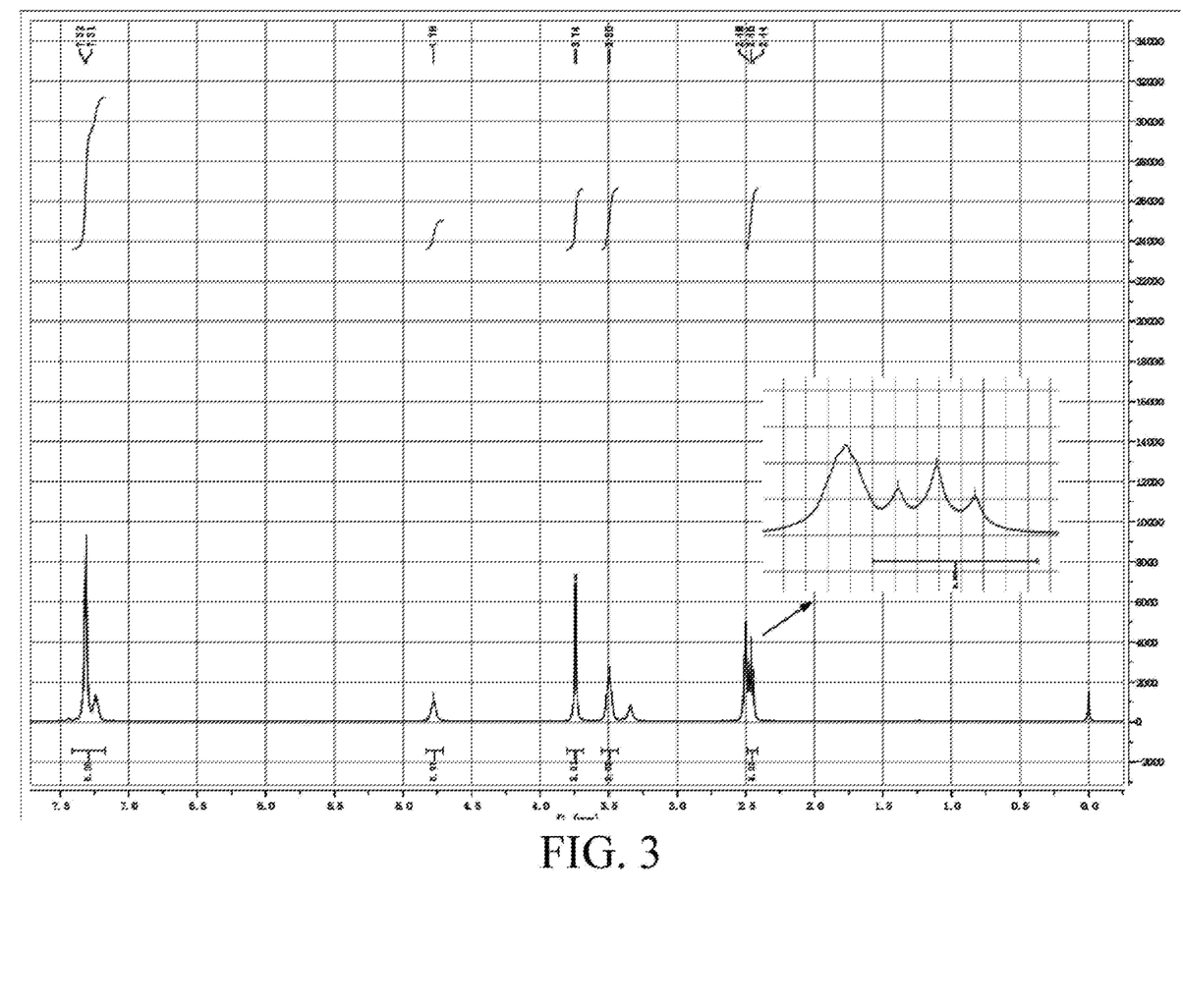
FIG. 3 is a $^1$H NMR of hydroxyethyl benzyl sulfide.
Figure 10:
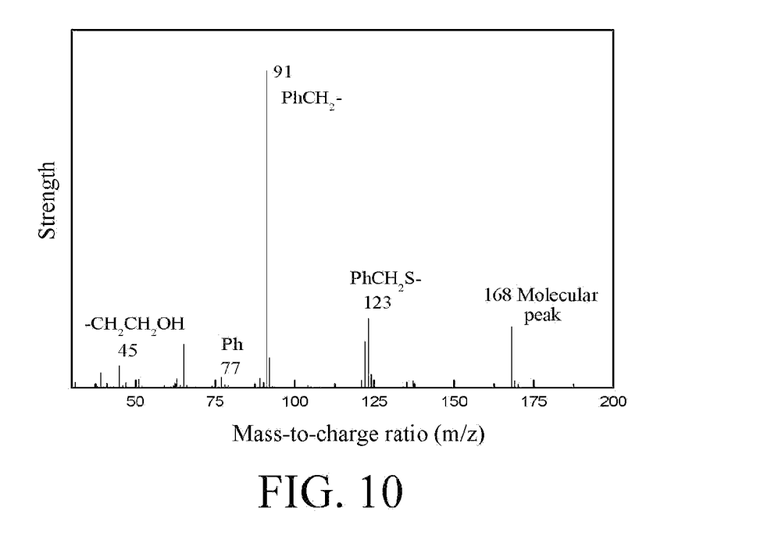
FIG. 10 is a GC-MS of hydroxyethyl benzyl sulfide.
Figure 11:
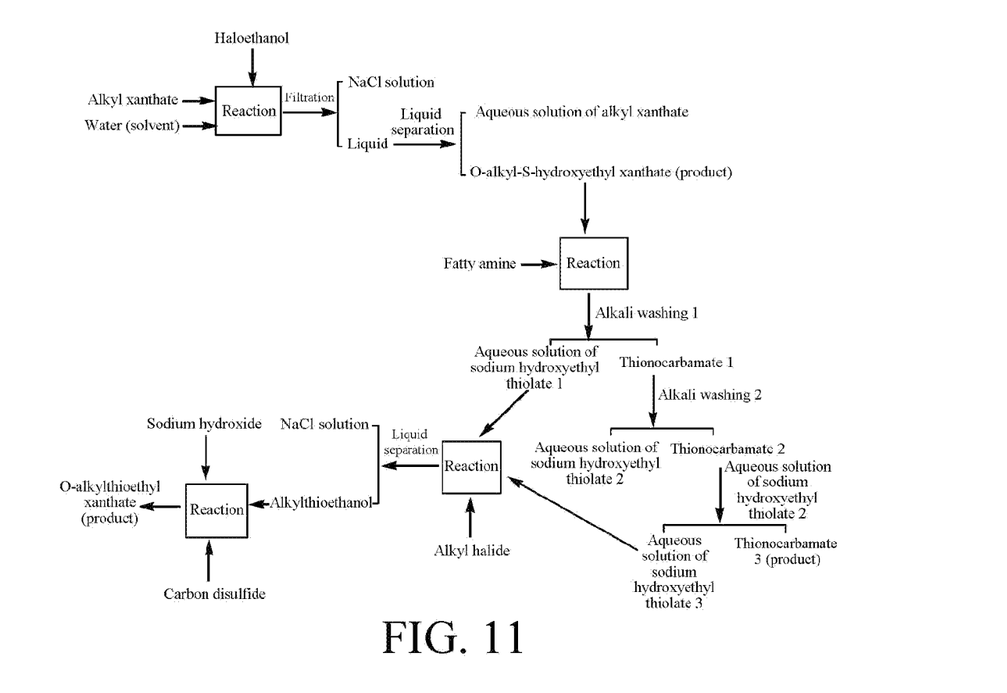
FIG. 11 is a process flow diagram of the present invention.

Example 5: Preparation of Hydroxyethyl Benzyl Sulfide 12.78 parts of benzyl chloride are added into 50 mL of aqueous solution containing 10.0 parts of sodium 2-hydroxyethyl thiolate, and the mixture reacts for 1 h at 10° C. to obtain an oil phase which is the hydroxyethyl benzyl sulfide with the purity of 89.97% and the yield of 96.5% based on the sodium 2-hydroxyethyl thiolate. The product is characterized after extraction, water washing and then purification, and $^1$H NMR of the hydroxyethyl benzyl sulfide is shown in FIG. 3, and a GC-MS is shown in FIG. 10.

Figure 4:
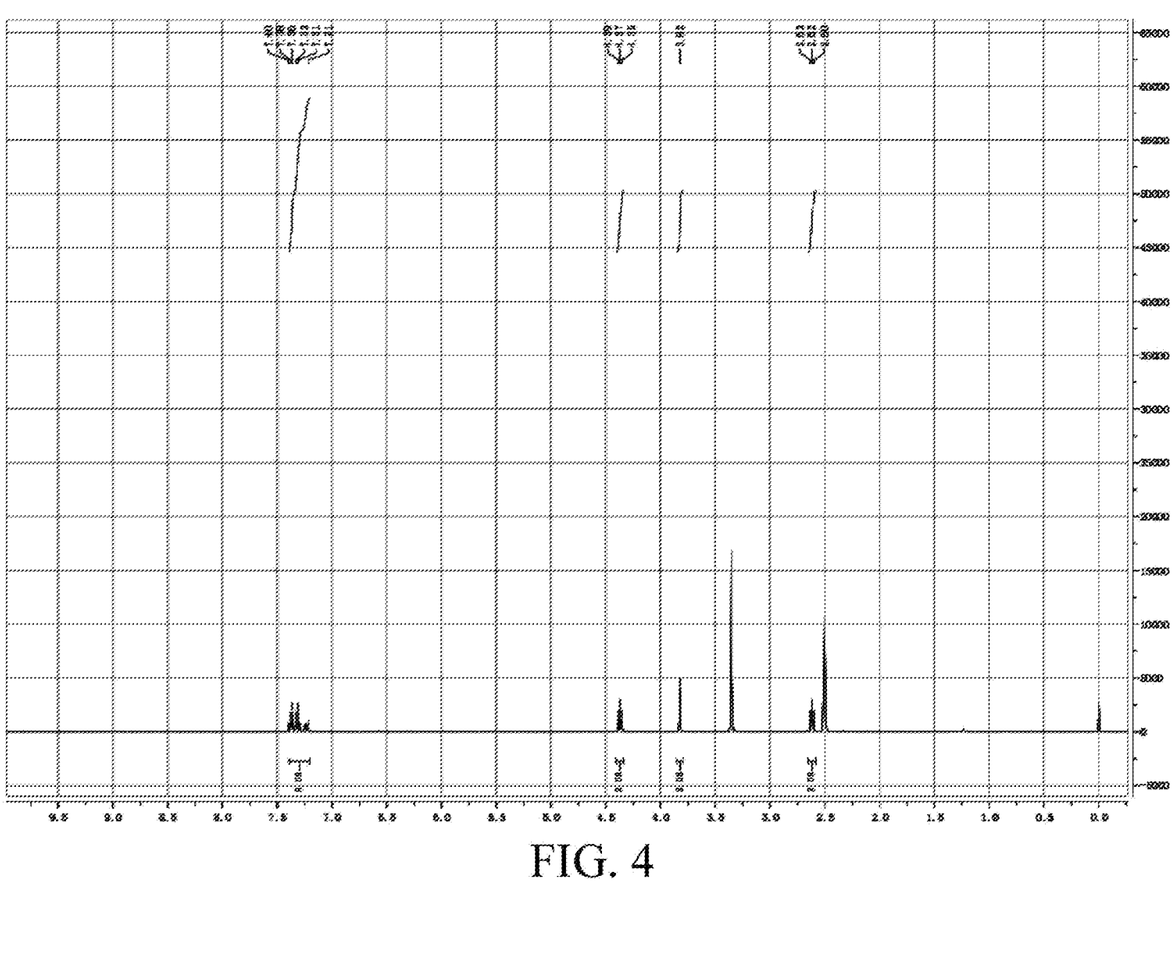
FIG. 4 is a $^1$H NMR of O-benzylthio ethyl xanthate.
Figure 8:
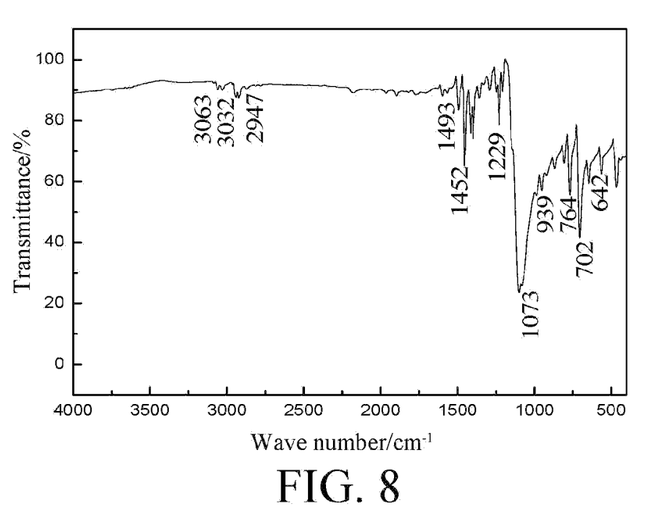
FIG. 8 is an infrared spectrogram of O-benzylthioethyl xanthate.

Example 6: Preparation of O-Benzylthio Ethyl Xanthate 18.67 parts of hydroxyethyl benzyl sulfide with the purity of 89.97% is transferred into a three-necked flask, 27.7 parts of carbon disulfide with the purity of 99% and 4.17 parts of sodium hydroxide with the purity of 96% are added into the three-necked flask, the reaction temperature is controlled at 25° C., and the reaction time is controlled to be 3 hours to obtain the O-benzylthio ethyl xanthate with the purity of 94.3% and the yield of 99.1% based on the hydroxyethyl benzyl sulfide. $^1$H NMR of the O-benzylthio ethyl xanthate after petroleum ether/acetone purification of the product is completed is shown in FIG. 4, and an infrared spectrogram is shown in FIG. 8.

$^1$H NMRs of parts of the foregoing prepared target products are shown in Table 1.

TABLE 1

| Analysis of 1H Nuclear Magnetic Resonance Spectrogram | |
|---|---|
| Compound | H-NMR/δ |
| O-isopropyl-S-hydroxyethyl xanthate (CDCl$_3$) | δ: 1.33(6H, —CH$_3$); 1.70(1H, —OH); 3.28(2H, —CH$_2$—); 3.82(2H, —CH$_2$—); 5.70(1H, CH). |
| O-isobutyl-S-hydroxyethyl xanthate (deuterated DMSO) | δ: 0.95(6H, —CH$_3$); 2.09(1H, CH); 3.22(2H, —CH$_2$—); 3.62(2H, —CH$_2$—); 4 36(2H, —CH$_2$—); 5.08(1H, —OH). |
| Hydroxyethyl benzyl sulfide (deuterated DMSO) | δ: 2.46(2H, —CH$_2$—); 3.50(2H, —CH$_2$—); 3.74(2H, —CH$_2$—); 4.78(1H, —OH); 7.31(5H, —C$_6$H$_5$). |
| O-benzylthio ethyl xanthate (deuterated DMSO) | δ: 2.62(2H, —CH$_2$—); 3.82(2H, —CH$_2$—); 4.37(2H, —CH$_2$—); 7.32(5H, —C$_6$H$_5$). |
| O-isopropyl-N-ethylcarbamate (CDCl$_3$) | δ: 1.23(6H, —CH$_3$); 1.30(3H, —CH$_3$); 3.47(2H, —CH$_2$—); 3.76(1H, NH); 5.46(1H, CH) |

Infrared analysis of parts of the foregoing prepared target products is shown in Table 2.

TABLE 2

| Infrared analysis of target products | |
|---|---|
| Compound | Peak shift and possible attribution |
| O-isopropyl-S-hydroxyethyl xanthate | 3363 cm$^{-1}$ is O—H stretching vibration; 2985 cm$^{-1}$ and 2872 cm$^{-1}$ are —CH$_3$ stretching vibration; 2928 cm$^{-1}$ is —CH$_2$— stretching vibration; 1234 cm$^{-1}$ is C—O—C stretching vibration; 1042 cm$^{-1}$ is C=S stretching vibration; and 934 cm$^{-1}$ is C—S stretching vibration. |
| O-isobutyl-S-hydroxyethyl xanthate | 3360 cm$^{-1}$ is O—H stretching vibration; 2963 cm$^{-1}$ and 2875 cm$^{-1}$ are —CH$_3$ stretching vibration; 2934 cm$^{-1}$ is —CH$_2$— stretching vibration; 1221 cm$^{-1}$ is C—O—C stretching vibration; 1061 cm$^{-1}$ is C=S stretching vibration; and 929 cm$^{-1}$ is C—S stretching vibration. |
| O-benzylthio ethyl xanthate | 3063 cm$^{-1}$ and 3032 cm$^{-1}$ are stretching vibration of C=C—H on a benzene ring; 2947 cm$^{-3}$ is —CH$_2$— stretching vibration; 1493 cm$^{-1}$ and 1452 cm$^{-1}$ are benzezne ring skeleton stretching vibration; 1229 cm$^{-1}$ is C—O—C stretching vibration; 1073 cm$^{-1}$ is C=S stretching vibration; 939 cm$^{-1}$ is C—S stretching vibration; and 764 cm$^{-1}$, 702 cm$^{-1}$ and 642 cm$^{-1}$ are benzene ring bending vibration. |

TABLE 2-continued

Infrared analysis of target products

| Compound | Peak shift and possible attribution |
|---|---|
| O-isopropyl-N-ethylthiocarbamate | 3265 cm$^{-1}$ is N—H stretching vibration; 2982 cm$^{-1}$ and 2877 cm$^{-1}$ are —CH$_3$ stretching vibration; 2928 cm$^{-1}$ is —CH$_2$— stretching vibration; 1530 cm$^{-1}$ is C—N stretching vibration; 1220 cm$^{-1}$ is C—O—C stretching vibration; 1053 cm$^{-1}$ is C=S stretching vibration; and 908 cm$^{-3}$ is C—S stretching vibration. |

Example 7: Flotation of Chalcopyrite by O-Isopropyl-S-Hydroxyethyl Xanthate

When the concentration of O-isopropyl-S-hydroxyethyl xanthate is 14 mg/L, the pH value of ore pulp is 6.5, the amount of a foaming agent (MIBC) is 15 mg/L and the rotating speed is 1992 r/min, chalcopyrite with the granularity of minus 0.076 mm to plus 0.038 mm is floated for 5 minutes, and the flotation recovery of the chalcopyrite is 97.94%.

Example 8: Flotation of Pyrite by O-Isopropyl-S-Hydroxyethyl Xanthate

When the concentration of the O-isopropyl-S-hydroxyethyl xanthate is 14 mg/L, the amount of a foaming agent (MIBC) is 15 mg/L and the rotating speed is 1992 r/min, pyrite with the granularity of minus 0.076 mm to plus 0.038 mm is floated for 5 minutes, the flotation recovery of the pyrite is 45.2% when the pH value of ore pulp is 2.0, and the flotation recovery of the pyrite is 15.3% when the pH value of the ore pulp is 6.5.

Example 9: Flotation of Chalcopyrite by O-Benzylthio Ethyl Xanthate

When the concentration of O-benzylthio ethyl xanthate is 5.3 mg/L, the amount of a foaming agent (MIBC) is 15 mg/L and the rotating speed is 1992 r/min, chalcopyrite with the granularity of minus 0.076 mm to plus 0.038 mm is floated for 5 minutes, and when the pH of ore pulp is 8.0, the flotation recovery of the chalcopyrite is 97.2%.

Example 10: Flotation Experiment of Porphyry Copper-Molybdenum Ores

A certain copper sulfide ore sample in Shangri-La contains 0.53% of copper, and the main copper ore is chalcopyrite.

When the grinding fineness of minus 200 meshes accounts for 64.5%, the dosage lime is 600 g/t, and the pH value of ore pulp is about 8.0; after a process of one-time roughing and one-time scavenging, the flotation result of the copper by butyl xanthate and the O-isopropyl-S-hydroxyethyl xanthate is shown in table 3, and the flotation result shows that the O-isopropyl-S-hydroxyethyl xanthate can achieve a comparable copper recovery rate under the condition of less use amount compared with the butyl xanthate. If the butyl xanthate is used in combination with the O-isopropyl-S-hydroxyethyl xanthate without MIBC, the copper recovery rate is greatly improved compared to the two reagents used alone.

TABLE 3

Copper ore flotation experimental conditions and results

| Reagent conditions (g/t) | Product | Yield (%) | Cu grade (%) | Cu recovery rate (%) |
|---|---|---|---|---|
| Roughing: butyl xanthate 50, MIBC 12; Scavenging: butyl xanthate 15, MIBC 4 | Rough concentrate | 3.93 | 11.35 | 83.59 |
| | Middlings | 2.54 | 1.35 | 6.43 |
| | Tailings | 93.53 | 0.057 | 9.98 |
| | Feed | 100 | 0.53 | 100.00 |
| Roughing: O-isopropyl-S-hydroxyethyl xanthate 32, MIBC 12; Scavenging: O-isopropyl-S-hydroxyethyl xanthate 8. | Rough concentrate | 7.74 | 5.95 | 83.37 |
| | Middlings | 3.67 | 1.03 | 6.84 |
| | Tailings | 85.59 | 0.061 | 9.79 |
| | Feed | 100 | 0.53 | 100.00 |
| Roughing: O-isopropyl-S-hydroxyethyl xanthate 16, butyl xanthate 30; Scavenging: butyl xanthate 15 | Rough concentrate | 7.24 | 6.29 | 88.96 |
| | Middlings | 1.33 | 1.00 | 2.62 |
| | Tailings | 91.43 | 0.047 | 8.42 |
| | Feed | 100 | 0.53 | 100.00 |

In the present invention, xanthate and 2-haloethanol are taken as initial raw materials to obtain the high-purity thionocarbamate, and meanwhile, the flotation collectors of O-alkyl/alkylthioethyl-S-hydroxyethyl xanthate and O-alkylthioethyl xanthate are co-produced. By comparison of flotation examples, it is found that O-alkyl/alkylthioethyl-S-hydroxyethyl xanthate has a higher flotation effect, a comparable flotation recovery rate can be achieved with a lower use amount of O-alkyl/alkylthioethyl-S-hydroxyethyl xanthate than conventional flotation for copper sulfide ores by the butyl xanthate, and the flotation recovery can be greatly increased when the butyl xanthate is used in combination with the O-alkyl/alkylthioethyl-S-hydroxyethyl xanthate. In the present invention, a plurality of products with high added values can be obtained by one process.

What is claimed is:
1. A method for preparing a thionocarbamate, comprising the following steps:
step 1): esterification reaction of a xanthate having a structure shown in formula I with 2-haloethanol to obtain an O-alkyl/alkylthioethyl-S-hydroxyethyl xanthate having a structure shown in formula II;
step 2): aminolysis reaction of the O-alkyl/alkylthioethyl-S-hydroxyethyl xanthate with a fatty amine shown in formula III to obtain a reaction mixture of a thionocarbamate shown in formula IV and 2-mercaptoethanol;
step 3): washing the reaction mixture obtained in step 2 with an alkali to convert the 2-mercaptoethanol in the reaction mixture to 2-hydroxyethyl thiolate, and separating the thionocarbamate as an oil phase from the 2-hydroxyethyl thiolate as an aqueous phase;

Formula I

Formula II

Formula III

Formula IV wherein, in formula I, M is Na$^+$, K$^+$ or NH$_4$$^+$; in formula I, formula II and formula IV, R$^1$ is C$_1$ to C$_{16}$ alkyl, C$_1$ to C$_{16}$ aryl, or alkylthioethyl shown in formula V; in formula III and formula IV, R$^2$ is C$_1$ to C$_8$ alkyl; and Formula V wherein, in formula V, R$^3$ is C$_1$ to C$_{16}$ alkyl or aryl.

2. The method according to claim 1, wherein the 2-haloethanol is 2-chloroethanol or 2-bromoethanol;
a molar ratio of the xanthate to the 2-haloethanol is 1.0:(0.9-1.2);
a solvent for the esterification reaction is water used at an amount of 0-50 ml per 1 mol of the xanthate;
the esterification reaction is conducted at a temperature of 20-100° C. for a reaction time of 1-8 h; and
the 2-haloethanol is reacted with the xanthate at 20-30° C. for 1-2 h before the water is added to the esterification reaction at 20-100° C.

3. The method according to claim 1, wherein
the aminolysis reaction in step 2) is conducted at a temperature of 30-100° C. for a reaction time of 1-6 h; and
the fatty amine is added at an amount of 0.9-1.2 times a molar weight of the O-alkyl/alkylthioethyl-S-hydroxyethyl xanthate.

4. The method according to claim 1, wherein in step 3), the reaction mixture of the thionocarbamate and the 2-mercaptoethanol is washed 1-5 times with the alkali having a concentration of 0.1-5 mol/L.

5. The method according to claim 1, further comprising: washing the 2-hydroxyethyl thiolate obtained in step 3), with an acid, to obtain a 2-mercaptoethanol product.

6. The method according to claim 1, further comprising: a thioalkylation reaction of the 2-hydroxyethyl thiolate obtained in step 3) with an alkyl halide having a structure shown in formula VI, to obtain a 2-alkylthioethanol having a structure shown in formula VII, and the 2-alkylthioethanol is reacted with carbon disulfide the alkali to obtain the O-alkylthioethyl xanthate as shown in formula VIII;

Formula V

Formula VI

Formula VII

Formula VIII wherein R$^1$ is C$_1$ to C$_8$ alkyl and aryl, or alkylthioethyl as shown in formula V; X is Cl, Br or I; and M is a cation of the alkali, wherein the cation of the alkali is Na$^+$ or K$^+$; or NH$_4$$^+$.

7. The method according to claim 6, wherein the thioalkylation reaction is conducted at a temperature of 5-50° C. for a reaction time of 0.5-3 h, and the alkyl halide is added at an amount of 0.8-1.3 times a molar weight of the 2-hydroxyethyl thiolate.

8. The method according to claim 6, wherein
to obtain the O-alkylthioethyl xanthate, the 2-alkylthioethanol is reacted with the carbon disulfide and the alkali at a temperature of 10-40° C. for a reaction time of 1-6 h, and a molar ratio of 1.0:(1.0-5.0):(0.9-1.2) of the 2-alkylthioethanol to the carbon disulfide to the alkali.

9. An O-alkylthioethyl xanthate collector prepared in the method according to claim 6, wherein the O-alkylthioethyl xanthate has a structure shown in formula VIII;

wherein R$^1$ is C$_1$ to C$_8$ alkyl and aryl, or alkylthioethyl as shown in formula V; X is Cl, Br or I; and M is a cation of the alkali, wherein the cation of the alkali is Na$^+$ or K$^+$; or NH$_4$.

10. A method of using the O-alkylthioethyl xanthate collector according to claim 9, wherein the O-alkylthioethyl xanthate collector is used in flotation separation of nonferrous metal sulfide ores.

11. The method according to claim 5, wherein the 2-haloethanol is 2-chloroethanol or 2-bromoethanol;
a molar ratio of the xanthate to the 2-haloethanol is 1.0:(0.9-1.2);
a solvent for the esterification reaction is water used at an amount of 0-50 ml per 1 mol of the xanthate;
the esterification reaction is conducted at a temperature of 20-100° C. for a reaction time of 1-8 h; and
the 2-haloethanol is reacted with the xanthate at 20-30° C. for 1-2 h before the water is added to the esterification reaction at 20-100° C.

12. The method according to claim 5, wherein
the aminolysis reaction in step 2 is conducted at a temperature of 30-100° C. for a reaction time of 1-6 h; and
the fatty amine is added at an amount of 0.9-1.2 times a molar weight of the O-alkyl/alkylthioethyl-S-hydroxyethyl xanthate.

13. The method according to claim 5, wherein in step 3), the reaction mixture of the thionocarbamate and the 2-mercaptoethanol is washed 1-5 times with the alkali having a concentration of 0.1-5 mol/L.

14. The method according to claim 6, wherein the 2-haloethanol is 2-chloroethanol or 2-bromoethanol;
a molar ratio of the xanthate to the 2-haloethanol is 1.0:(0.9-1.2);
a solvent for the esterification reaction is water used at an amount of 0-50 ml per 1 mol of the xanthate;
the esterification reaction is conducted at a temperature of 20-100° C. for a reaction time of 1-8 h; and
the 2-haloethanol is reacted with the xanthate at 20-30° C. for 1-2 h before the water is added to the esterification reaction at 20-100° C.

15. The method according to claim 6, wherein the aminolysis reaction in step 2 is conducted at a temperature of 30-100° C. for a reaction time of 1-6 h; and the fatty amine is added at an amount of 0.9-1.2 times a molar weight of the O-alkyl/alkylthioethyl-S-hydroxyethyl xanthate.

16. The method according to claim 6, wherein in step 3), the washing the reaction mixture obtained in step 2 is performed 1-5 times with the alkali having a concentration of 0.1-5 mol/L.

* * * * *